(12) United States Patent
Huang et al.

(10) Patent No.: US 8,137,529 B2
(45) Date of Patent: Mar. 20, 2012

(54) METHODS OF USING AN ELECTROCHEMICAL BIOSENSOR

(75) Inventors: Dijia Huang, Granger, IN (US); Steven C. Charlton, Osceola, IN (US); Suny J. George, Granger, IN (US); Andrew J. Edelbrock, Granger, IN (US)

(73) Assignee: Bayer HealthCare LLC, Tarrytown, NY (US)

(*) Notice: Subject to any disclaimer, the term of this patent is extended or adjusted under 35 U.S.C. 154(b) by 0 days.

(21) Appl. No.: 12/949,645

(22) Filed: Nov. 18, 2010

(65) Prior Publication Data

US 2011/0061458 A1     Mar. 17, 2011

Related U.S. Application Data

(62) Division of application No. 10/590,834, filed as application No. PCT/US2005/004226 on Feb. 4, 2005, now Pat. No. 7,862,695.

(60) Provisional application No. 60/542,364, filed on Feb. 6, 2004.

(51) Int. Cl.
| | |
|---|---|
| *G01N 27/26* | (2006.01) |
| *G01N 27/327* | (2006.01) |
| *G01F 23/00* | (2006.01) |
| *G01R 27/26* | (2006.01) |

(52) U.S. Cl. ............... 205/777.5; 205/779; 205/792; 205/775; 205/787; 702/23; 73/149; 324/662; 324/663; 324/664

(58) Field of Classification Search ............ 204/401, 204/403.1–403.14, 409, 406.06, 412, 411, 204/416–418; 205/775, 778, 792, 789, 775.5, 205/777.5, 787, 779; 324/662–664; 73/149; 702/23

See application file for complete search history.

(56) References Cited

U.S. PATENT DOCUMENTS

| | | | |
|---|---|---|---|
| 4,172,770 A | 10/1979 | Semersky et al. | 204/1 T |
| 4,549,952 A | 10/1985 | Columbus | 204/416 |
| 5,120,420 A | 6/1992 | Nankai et al. | 204/403 |
| 5,141,868 A | 8/1992 | Shanks et al. | 435/288 |
| 5,192,415 A | 3/1993 | Yoshioka et al. | 204/403 |
| 5,264,103 A | 11/1993 | Yoshioka et al. | 204/403 |
| 5,352,351 A | 10/1994 | White et al. | 204/406 |
| 5,512,159 A | 4/1996 | Yoshioka et al. | 204/403 |
| 5,575,403 A | 11/1996 | Charlton et al. | 221/31 |

(Continued)

FOREIGN PATENT DOCUMENTS

CA       2419213 A1    6/2011

(Continued)

OTHER PUBLICATIONS

Written Opinion corresponding to International Patent Application No. PCT/US2005/004226, European Patent Office, dated Jun. 8, 2005, 6 pages.

(Continued)

*Primary Examiner* — Jeffrey T Barton
*Assistant Examiner* — Jennifer Dieterle
(74) *Attorney, Agent, or Firm* — Nixon Peabody LLP

(57) ABSTRACT

According to one embodiment of the present invention, an electrochemical sensor (10) for detecting the concentration of analyte in a fluid test sample is disclosed. The sensor (10) includes a counter electrode having a high-resistance portion for use in detecting whether a predetermined amount of sample has been received by the test sensor.

24 Claims, 5 Drawing Sheets

U.S. PATENT DOCUMENTS

| | | | |
|---|---|---|---|
| 5,582,697 A | 12/1996 | Ikeda et al. | 204/403 |
| 5,620,579 A | 4/1997 | Genshaw et al. | 204/402 |
| 5,628,890 A | 5/1997 | Carter et al. | 204/403 |
| 5,653,863 A | 8/1997 | Genshaw et al. | 205/777.5 |
| 5,759,364 A | 6/1998 | Charlton et al. | 204/403.14 |
| 5,786,584 A | 7/1998 | Button et al. | 235/462 |
| 5,798,031 A * | 8/1998 | Charlton et al. | 204/403.14 |
| 6,518,034 B1 | 2/2003 | Phillips et al. | 435/14 |
| 6,531,040 B2 | 3/2003 | Musho et al. | 204/401 |
| 6,814,844 B2 * | 11/2004 | Bhullar et al. | 204/403.01 |
| 6,841,052 B2 * | 1/2005 | Musho et al. | 204/401 |
| 7,118,668 B1 | 10/2006 | Edelbrock et al. | 205/777.5 |
| 7,122,110 B2 | 10/2006 | Deng et al. | 205/777.5 |
| 7,125,481 B2 | 10/2006 | Musho et al. | 205/775 |
| 2001/0042683 A1 * | 11/2001 | Musho et al. | 204/403 |
| 2002/0175075 A1 * | 11/2002 | Deng et al. | 204/403.01 |

FOREIGN PATENT DOCUMENTS

| | | |
|---|---|---|
| DE | 197 47 875 A1 | 5/1999 |
| EP | 0 429 076 A2 | 5/1991 |
| EP | 0 502 504 A1 | 9/1992 |
| EP | 0537761 | 4/1993 |
| EP | 0 636 879 A2 | 2/1995 |
| EP | 0 679 720 A1 | 11/1995 |
| EP | 0 732 406 A1 | 9/1996 |
| EP | 0 735 363 A1 | 10/1996 |
| EP | 0 795 601 A2 | 9/1997 |
| EP | 0 795 748 A1 | 9/1997 |
| EP | 0 800 080 A2 | 10/1997 |
| EP | 0 851 224 A1 | 7/1998 |
| EP | 0 872 728 A1 | 10/1998 |
| EP | 0 877 244 A1 | 11/1998 |
| EP | 0 909 952 A2 | 4/1999 |
| EP | 1 074 335 A2 | 2/2001 |
| EP | 1 074 832 A1 | 2/2001 |
| EP | 1 081 490 A1 | 3/2001 |
| GB | 2 296 332 A | 6/1996 |
| JP | 5-502727 | 5/1993 |
| JP | 6109688 | 4/1994 |
| JP | 1-932654 | 5/1995 |
| JP | 8-502589 | 3/1996 |
| JP | 08-304340 | 11/1996 |
| JP | 8-320304 | 12/1996 |
| JP | 9-222411 | 8/1997 |
| JP | 10-318970 | 12/1998 |
| JP | 2960265 B2 | 10/1999 |
| JP | 2001-066279 | 3/2001 |
| JP | 2003-004691 | 1/2003 |
| JP | 2003-014684 | 1/2003 |
| WO | WO 99/60391 | 11/1999 |

OTHER PUBLICATIONS

International Search Report corresponding to International Patent Application No. PCT/US2005/004226, European Patent Office, dated Jun. 8, 2005, 5 pages.

* cited by examiner

METHODS OF USING AN ELECTROCHEMICAL BIOSENSOR

CROSS-REFERENCE TO RELATED APPLICATIONS

This application is a divisional of U.S. patent application Ser. No. 10/590,834, titled "Electrochemical Biosensor," and filed on Aug. 24, 2006, now allowed, which is a U.S. national stage of International Application No. PCT/US2005/04226, titled "Electrochemical Biosensor," and filed Feb. 4, 2005, which claims priority to Application No. 60/542,364, titled "Electrochemical Biosensor," and filed on Feb. 6, 2004, each of which is incorporated by reference in its entirety.

FIELD OF THE INVENTION

The present invention is generally related to an electrochemical biosensor for use in the quantification of an analyte in a liquid sample and, more particularly, to a system for detecting an insufficient sample amount in an electrochemical biosensor.

BACKGROUND OF THE INVENTION

Medical conditions such as diabetes require a person afflicted with the condition to regularly self-monitor that person's blood-glucose concentration level. The purpose of monitoring the blood glucose concentration level is to determine the person's blood glucose concentration level and then to take corrective action, based upon whether the level is too high or too low, to bring the level back within a normal range. The failure to take corrective action can have serious medical implications for that person.

One method of monitoring a person's blood glucose level is with a portable testing device. The portable nature of these devices enables users to conveniently test their blood glucose levels wherever they may be. One type of device utilizes an electrochemical biosensor to harvest the blood sample and to analyze the blood sample. The electrochemical biosensor includes a reagent designed to react with glucose in the blood to create an oxidation current at electrodes disposed within the electrochemical biosensor—this current is indicative of the user's blood glucose concentration level.

A predetermined amount of reagent is included within an electrochemical biosensor, and is designed to react with a predetermined sample volume. If a less-than required sample volume is harvested by the electrochemical biosensor—a condition referred to as being under-filled—an erroneous measurement may result. Because electrochemical biosensors are commonly used in a self-testing environment, there exists an increased chance that an inappropriate amount of sample may be collected. Further, because the sample volumes are very small (typically less than about 10 µl) it is difficult for a user to visually determine whether an appropriate amount of sample has been harvested for analysis. Thus, there exists a need for an electrochemical biosensor that reliably detects and alerts a user to the occurrence of an under-filled condition.

SUMMARY OF THE INVENTION

According to one embodiment of the present invention, an electrochemical sensor for detecting the concentration of analyte in a fluid test sample is disclosed. The sensor includes a counter electrode having a high-resistance portion for use in detecting whether a predetermined amount of sample has been received by the test sensor.

According to another embodiment of the present invention, a method for evaluating whether an electrochemical test sensor is properly filled is disclosed. The test sensor includes a working electrode coupled to a first lead and a counter electrode coupled to a second lead. The counter electrode includes a high-resistance portion and a low-resistance portion. The test sensor includes a reagent disposed on the working electrode that is adapted to react with an analyte in a fluid sample for producing an electrochemical reaction indicative of the concentration of the analyte in the fluid sample. The method comprises applying a voltage profile across the first and second leads, measuring the current profile at the first and second leads in response to the applied voltage profile, and generating an under-filled error signal when the measured current profile does not have a predetermined profile.

The above summary of the present invention is not intended to represent each embodiment, or every aspect, of the present invention. Additional features and benefits of the present invention are apparent from the detailed description, figures, and embodiments set forth below.

Figure 1:
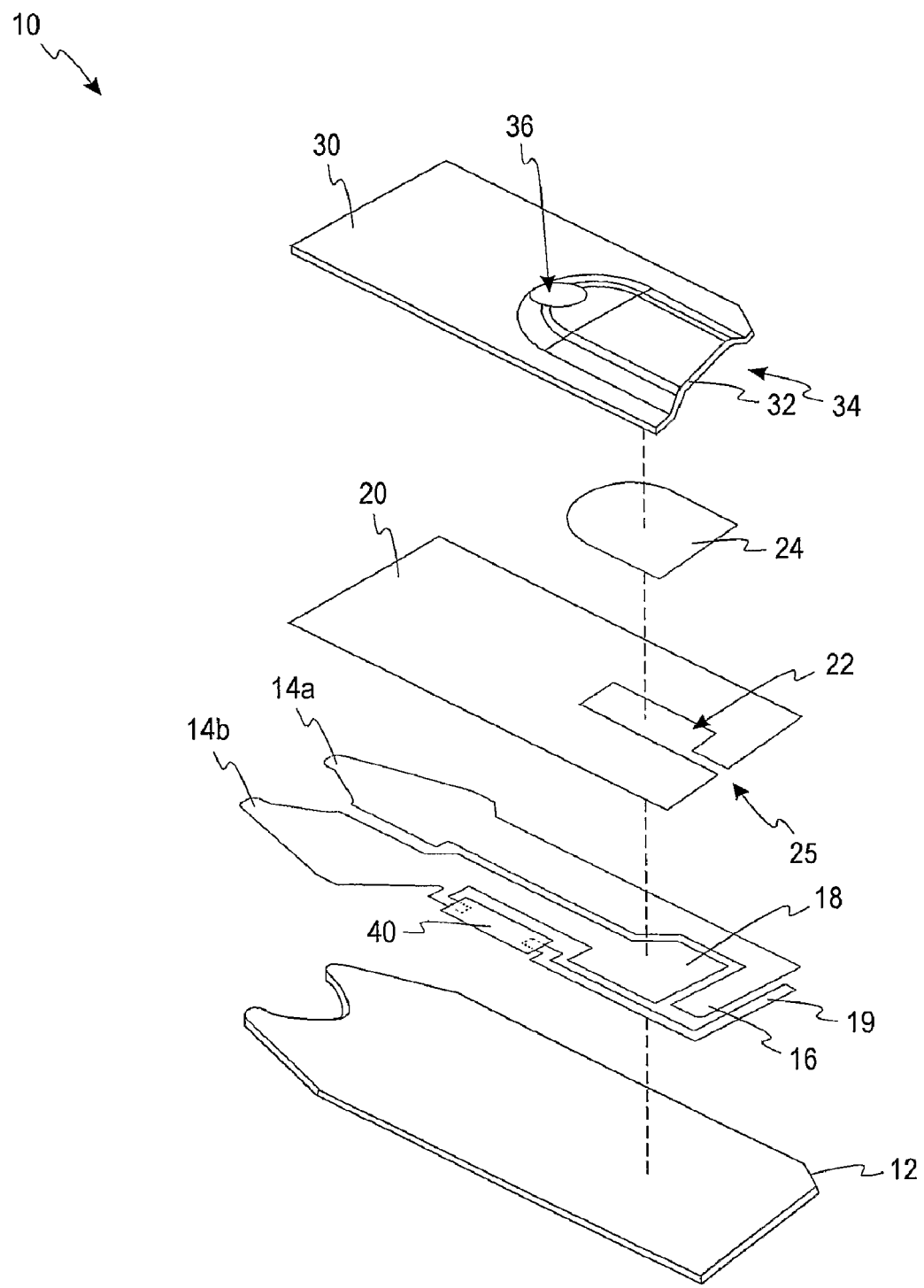
FIG. 1 is an exploded view of an electrochemical biosensor according to one embodiment of the present invention.

While the invention is susceptible to various modifications and alternative forms, specific embodiments are shown by way of example in the drawings and are described in detail herein. It should be understood, however, that the invention is not intended to be limited to the particular forms disclosed.

DETAILED DESCRIPTION OF THE ILLUSTRATED EMBODIMENTS

Turning to the drawings and initially to FIG. 1, the construction of an electrochemical sensor 10 is shown according to one embodiment of the present invention. The sensor 10 comprises an insulating base 12 upon which is printed in sequence (typically by screen printing techniques) an electrical conductor pattern including first and second leads 14a,b, an electrode pattern including a working electrode 16, a counter electrode, an insulating (dielectric) layer 20 including an opening 22 and a channel 25, and a reaction layer 24.

The counter electrode includes a low-resistance counter electrode branch 18 (LRC electrode) and a high-resistance counter electrode branch 19 (HRC electrode).

The reaction layer 24 includes a reagent for converting an analyte of interest (e.g., glucose) in a fluid test sample (e.g., blood) into a chemical species that is electrochemically measurable, in terms of the electrical current it produces, by the components of the electrode pattern. The reagent of the reaction layer 24 typically contains an enzyme such as, for example, glucose oxidase, which reacts with the analyte and with an electron acceptor such as a ferricyanide salt to produce an electrochemically measurable species that can be detected by the electrode pattern 16,18,19. The reaction layer 24 comprises a polymer, an enzyme, and an electron acceptor. The reaction layer 24 also includes additional ingredients such as a buffer and a surfactant in some embodiments of the present invention. The reaction layer 24 is disposed over the opening 22 and channel 25 in the insulating layer 20. Thus, the portion of the reaction layer 24 exposed to the electrode pattern 16,18,19 is defined by an opening 22 and a channel 25 in the insulating layer 20. The working electrode 16 is electrically coupled to the first lead 14a, and the LRC electrode 18 and HRC electrode 19 are electrically coupled to a second lead 14b.

The reaction layer 24 covers only the working electrode 16, covers the working electrode 16 and the LRC electrode 18, or covers the working electrode 16, the LRC electrode 18, and the HRC electrode 19 in alternative embodiments of the present invention. When the reaction layer 24 covers only the working electrode 16, an electroactive material is present on the LRC electrode 18 to allow it to function as a counter electrode as is well known in the art.

The sensor 10 includes a lid 30 having a concave portion 32 that forms a capillary channel when mated with the insulating layer 20 for moving the liquid sample from an inlet 34 into the test sensor 10. The downstream end of the capillary channel includes one or more openings 36 for venting the capillary channel—the fluid sample flows from the inlet 34 into the sensor 10 toward the opening 36. In use, the sensor 10 collects a fluid sample (e.g., a blood sample from a patient's finger) by bringing the capillary channel inlet 34 into contact with the fluid sample.

Figure 2A:
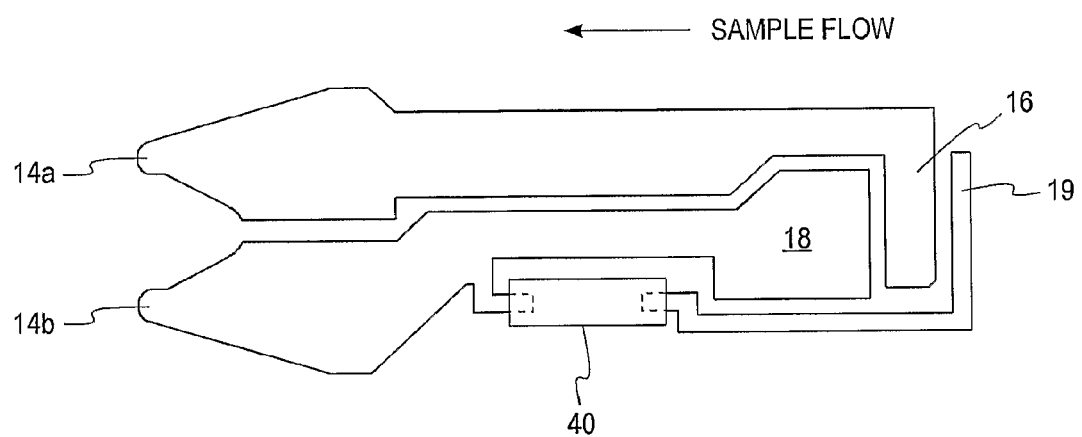
FIG. 2a is an oversized top view of an electrode pattern of the electrochemical bio sensor of FIG. 1.

Referring to FIG. 2a, the working electrode 16 and LRC electrode 18 are configured in a manner such that the LRC electrode 18 is located downstream (in terms of the direction of fluid sample flow along the flow path) from the working electrode 16. This configuration offers the advantage of requiring the test fluid to completely cover the working electrode 16 in order to contact the LRC electrode 18. However, the HRC electrode 19, which is coupled to the LRC electrode 18 via a resistor 40, is positioned upstream from the working electrode 16. According to one embodiment of the present invention, the resistor 40 has a resistance of about 50 kΩ to about 500 kΩ. In other embodiments, the resistance of the resistor 40 ranges between about 250 kΩ to about 350 kΩ. In yet another embodiment, the resistor 40 has a resistance of about 300 kΩ. The resistor 40 may be screen-printed on the insulating base 12 in a manner similar to the working electrode 16, the LRC electrode 18, the HRC electrode 19, and the leads 14a,b. Generally, as described below, the resistor 40 is used in detecting an under-filled condition in the test sensor 10, which can result in an inaccurate measurement of the analyte of interest in the fluid sample.

Figure 2B:
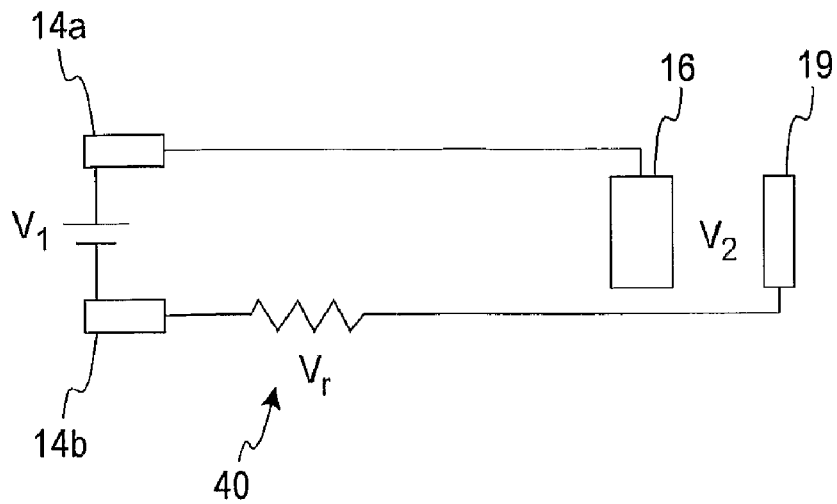
FIG. 2b is a circuitry schematic of the electrochemical biosensor of FIG. 2a when the electrochemical biosensor is partially filled with liquid sample.

Referring to FIG. 2b, the working electrode 16 and HRC electrode 19 form the circuit illustrated if the sensor 10 is under-filled (i.e., the LRC electrode 18 in FIG. 2a is not covered by the fluid sample). In this situation, the sensor current passes through the resistor 40. Thus, the potential $V_2$ between the working electrode 16 and the HRC electrode 19 is about the difference between the potential $V_1$ applied to the sensor leads 14a,b and the voltage drop $V_r$ across the resistor 40, assuming a negligible resistance along the electrode/lead pattern.

Figure 2C:
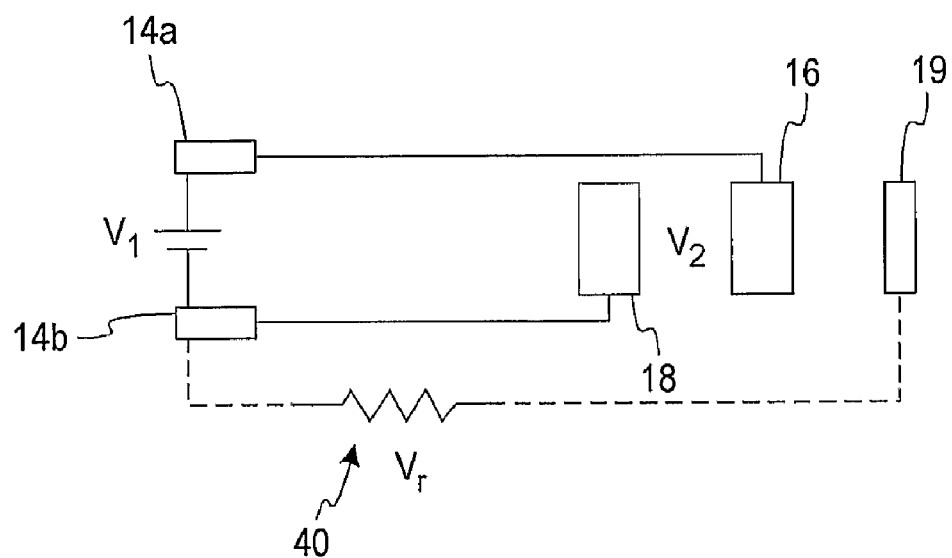
FIG. 2c is a circuitry schematic of the electrochemical biosensor of FIG. 2a when the electrochemical biosensor is appropriately filled with liquid sample.

Referring to FIG. 2c, the working electrode 16 and the LRC electrode 18 form the illustrated circuit if the sensor 10 is appropriately filled (i.e., the LRC electrode 18 in FIG. 2a is covered by the liquid sample). In this situation, the resistor 40 is electrically bypassed in the circuitry. Thus, the potential $V_2$ between the working electrode 16 and the LRC electrode 18 is substantially the same as the potential $V_1$ applied to the leads 14a,b of the sensor 10, assuming a negligible resistance along the electrode/lead pattern. The current measured in the sensor 10 is a result of diffusion of electro-active species to the electrodes and the subsequent redox reactions there. For example, at the working electrode 16 an electron is taken from ferrocyanide, oxidizing it to ferricyanide. At the LRC electrode 18 (or at the HRC electrode 19 in an under-filled situation), an electron is added to ferricyanide, reducing it to ferrocyanide. The flow of electrons in the electrical pattern connecting the two electrodes is measured and is related to the amount of ferrocyanide and hence to the amount of glucose in the sample. In normal operation, a relatively high electrical potential, $V_2$ in FIG. 2c, is applied between the electrodes (e.g., about 400 mV), making the oxidation and reduction reactions at the electrodes fast and depleting the region around the working electrode 16 of the reduced mediator (e.g., ferrocyanide). Thus, the current is not constant but decays with time as the reaction is limited by the diffusion to the electrode surface of the reduced mediator. In general, such decaying current i can be described according to equation (1):

$$i = C \cdot G \cdot t^{-k} \quad (1)$$

In equation (1), C is a constant, G is the concentration of the analyte (e.g., glucose) in the liquid sample, t is the time elapsed since the potential $V_2$ is applied, and k is a constant relating to the current decay profile.

If a higher electrical potential is applied, no increase in the sensor current is measured, and no change to the decay with time is measured because the sensor current is determined by diffusion to the electrode surface. If a lower electrical potential (e.g., about 200 mV) is applied between the electrodes, the oxidation and reduction reactions are slower, but fast enough that the sensor current remains dependent on diffusion. Eventually at a lower voltage (e.g., less than about 200 mV), local depletion of reduced mediator does not occur and the sensor current ceases to vary with time. Thus, during normal operation of the sensor 10, no change in the current decay profile occurs with time over a range of applied potentials.

The operation of the test sensor 10 with under-fill detection will be described. If the sensor 10 is under-filled (i.e., less than a requisite amount for the designed reaction) the sample only covers the HRC electrode 19 and at least a portion of the working electrode 16. In this under-filled situation, the HRC electrode 19 serves as the entire counter electrode with a high-resistance due to the resistor 40. FIG. 2b illustrates the circuit under this condition. Current flow through the resistance 40 causes a potential drop $V_r$ over the resistor 40 and reduces the potential $V_2$ available for the electrochemical reactions. If the resistance is high enough, the potential $V_2$ is reduced to a point where the electrode surface reactions are slow and the current measured between electrode leads 14a and 14b does not decay normally with time but is essentially flat. This flat equilibrium current is a dynamic balance between the sensor current and voltage drop $V_r$ on the resistor. Changing the applied voltage $V_1$ changes this equilibrium current—a lower voltage results in a lower equilibrium or steady-state current and a higher voltage results in a higher current. The sensor current has a "step" profile if a step-shaped voltage profile is applied.

In the situation where the sensor 10 is appropriately filled, the sample covers the LRC electrode 18, in addition to the HRC electrode 19, and the working electrode 16. FIG. 2c illustrates the circuitry under this condition. The branch of the circuitry between the HRC electrode 19 and the resistor 40 to the lead 14b is electrically bypassed by the direct connection between the LRC electrode 18 and the lead 14b. The working electrode 16 and the LRC electrode 18 form a low-resistance circuit, and the sensor current has a decay-type profile where the current is limited by diffusion of electro-active species to the electrode surface as described above.

The present invention provides an electrochemical sensor in which the electrodes are configured so that in the event of an under-filled condition, the result is a current response with time and/or applied voltage that is characteristic, and can be distinguished from the response of a correctly-filled sensor. Specifically, there are at least two ways in which to distinguish a partially-filled sensor 10 from a sensor 10 that is appropriately filled according to alternative embodiments of the present invention. First, the sensor current of a partially-filled sensor 10 does not decay normally with time, unlike the sensor current of an appropriately-filled sensor 10. Second, the sensor current of a partially-filled test sensor 10 increases with applied voltage due to the resistor 40, while the sensor current of an appropriately-filled sensor 10 (which bypasses the resistor) does not.

Thus, when the amount of test fluid that enters the capillary space of the test sensor 10 is sufficient only to cover the HRC electrode 19 and at least a portion of the working electrode 16, and when a suitable potential is applied, the current measured across leads 14a,b is essentially constant and not decay normally with time. Put another way, a device coupled to the leads 14a,b senses certain characteristics of the sensor current over time, which are used to determine if an under-filled error condition has occurred. This is accomplished by algorithmically programming the device to detect the under-filled condition by measuring the current at definite time periods after the test fluid has electrically connected the HRC electrode 19 with the working electrode 16, and/or after the test fluid has electrically connected the working electrode 16 with the LRC electrode 18.

Figure 3A:
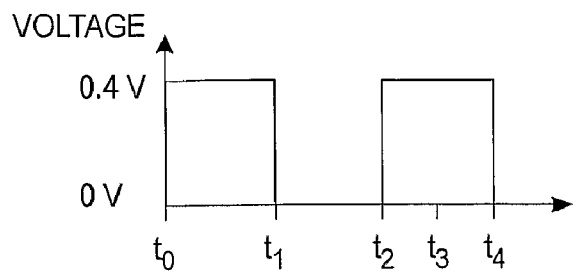
FIG. 3a is a plot of the voltage profile applied to the test sensor of FIG. 1 according to one embodiment of the present invention.
Figure 3B:
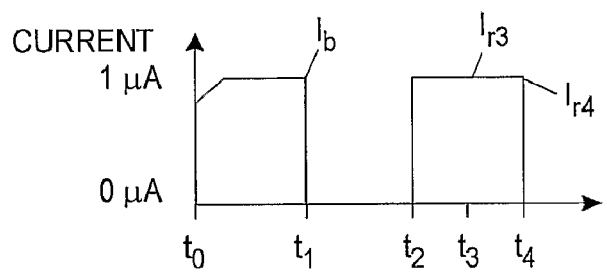
FIGS. 3b and 3c are plots of the current profile of the test sensor in response to the voltage profile of FIG. 3a in an under-filled condition and an appropriately-filled condition, respectively.
Figure 3C:
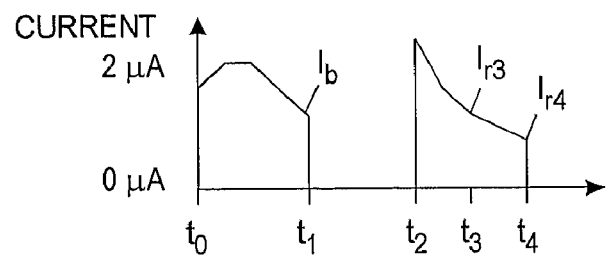

Referring to FIGS. 3a, 3b, and 3c, one method for determining whether the test sensor 10 is appropriately filled will be described. At time $t_0$, a voltage step is applied between the leads 14a,b and held constant until time $t_1$, this period is referred to as the burn period. Next, no voltage (e.g., an open circuit) is applied during a wait period from time $t_1$ to time $t_2$. Finally, the voltage step is again applied during a read period from $t_2$ to $t_4$. According to one embodiment of the present invention, the burn, wait, and read periods are each about 2 to about 10 seconds in duration. The applied step voltage is about 0.3 Volts to about 0.4 Volts, according to one embodiment of the present invention.

An under-filled sensor 10 generates a flat sensor current profile during the read period as shown, for example, in FIG. 3b. An appropriately-filled sensor 10 generates a typical decay-type sensor current profile during the read period as shown, for example, in FIG. 3c.

The decay factor, k, during the read period—from time $t_2$ to $t_4$—is calculated from the two currents, $I_{r3}$ and $I_{r4}$, measured at $t_3$ and $t_4$, according to equation (2):

$$k = \frac{\ln(I_{r3}) - \ln(I_{r4})}{\ln(t_4) - \ln(t_3)} \quad (2)$$

In equation (2), the decay factor, k, describes how fast the current i decays in equation (1), where C is a constant, G is the glucose concentration, and t is the time elapsed after the voltage is initially applied. In an appropriately-filled sensor 10, k is typically between about 0.30 and about 0.49, decreasing as glucose concentration increases. The decay factor drops to zero in under-filled conditions. Therefore, an under-filled sensor 10 is detected by checking if the decay factor is below a pre-determined lower limit.

Figure 4A:
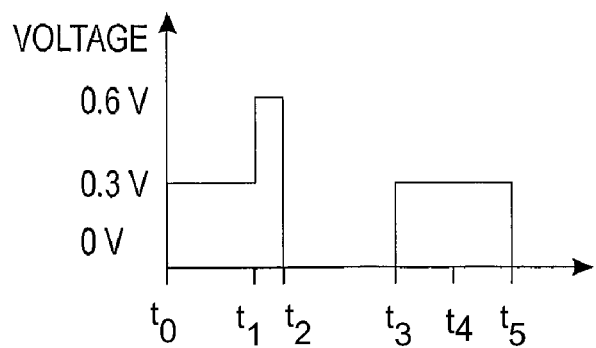
FIG. 4a is a plot of the voltage profile applied to the test sensor of FIG. 1 according to another embodiment of the present invention.
Figure 4B:
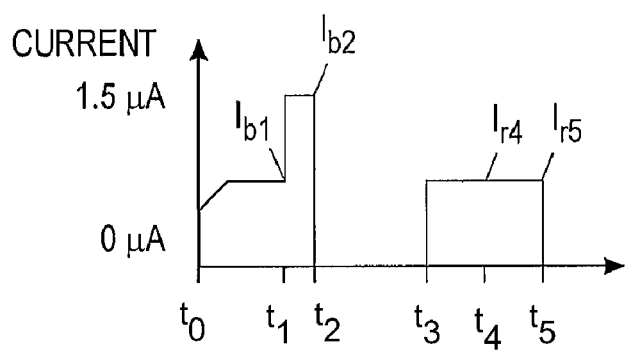
FIGS. 4b and 4c are plots of the current profile of the test sensor in response to the voltage profile of FIG. 4a in an under-filled condition and an appropriately-filled condition, respectively.
Figure 4C:
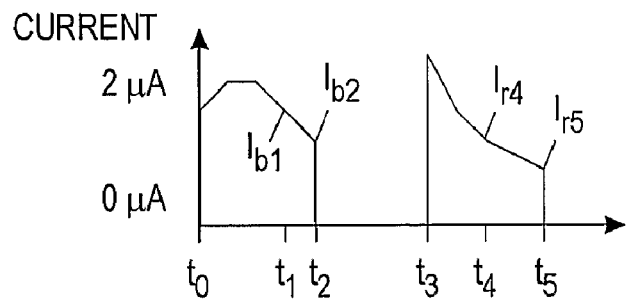

Referring to FIGS. 4a, 4b, and 4c, another method for determining whether the test sensor 10 is appropriately filled will be described. A first voltage is applied during the burn period occurring from time $t_0$ to time $t_1$, and a second higher voltage is applied until time $t_2$. No voltage is applied (e.g., an open circuit) during the wait period from time $t_2$ to time $t_3$. Finally, a voltage is applied during the read period from time $t_3$ to time $t_5$. According to one embodiment, the first voltage applied during the burn period from time $t_0$ to $t_1$ is about 0.3 V, and the second applied during the burn period from time $t_1$ to time $t_2$ is about 0.6 V. During the read period, a voltage of about 0.3 V is applied. The burn, wait, and read periods are each about 2 seconds to about 10 seconds in length, with the first voltage of the burn period applied for about 25% to about 75% of the total burn period, according to one embodiment of the present invention.

An under-filled sensor 10 generates a step sensor current profile $I_b$ during the burn period as shown, for example, in FIG. 4b. An appropriately-filled sensor 10 generates a decay-shaped sensor current profile as shown, for example, in FIG. 4c.

The decay factor k during the burn period is calculated from the two currents, $I_{b1}$ and $I_{b2}$, measured at $t_1$ and $t_2$, respectively, according to equation (3):

$$k = \frac{\ln(I_{b1}) - \ln(I_{b2})}{\ln(t_2) - \ln(t_1)} \quad (3)$$

During the burn period the decay factor is greater than about 0.2 in an appropriately-filled sensor, but drops below about −1.0 in an under-filled condition. Thus, an under-filled condition is detected by comparing the actual decay factor to a pre-determined lower limit during the burn period.

According to alternative embodiments, the two algorithms—equations (2) and (3)—for detecting an under-filled condition discussed in connection with FIGS. 3a-c and 4a-c are used jointly to determine whether an under-filled condition has occurred. The decay factor is first evaluated during the burn period as described in connection with FIGS. 4a-c. If no under-filled condition is determined, the decay factor is then evaluated during the read period as described in connection with FIGS. 3a-c. If no under-filled condition is detected during the burn and read periods, an appropriately-filled condition is deemed to have occurred.

While the invention is susceptible to various modifications and alternative forms, specific embodiments thereof are shown by way of example in the drawings and described in detail herein. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A method for evaluating whether an electrochemical sensor is properly filled, the electrochemical sensor including a working electrode and a counter electrode, the counter electrode including a high-resistance portion and a low-resistance portion, the high-resistance portion including a resistor, the method comprising:

introducing the fluid test sample to the electrochemical test sensor;

applying a first potential between a counter electrode and a working electrode for a first predetermined time period after the fluid test sample has electrically connected the working electrode and the counter electrode;

after the first predetermined time period, applying a second potential between the counter electrode and the working electrode for a second predetermined time period, the second potential having a magnitude that is greater than a magnitude of the first potential;

measuring the current between the counter electrode and the working electrode at a first interval during the first predetermined time period to obtain a first current measurement;

measuring the current between the counter electrode and the working electrode at a second interval during the second predetermined period to obtain a second current measurement;

determining a first parameter based on the first current measurement and the second current measurement;

comparing the first parameter to at least one first predetermined parameter; and notifying a user that an insufficient quantity of fluid test sample has been introduced to the electrochemical test sensor based on the comparing the first parameter to the at least one first predetermined parameter.

2. The method of claim 1, wherein the first parameter is determinable by a calculation having the general form $$\text{first parameter} = \ln(I_{t1}) - \ln(I_{t2})/(\ln(t2) - \ln(t1))$$

where $I_{t1}$ is the first current measurement at the first interval, t1, and $I_{t2}$ is the second current measurement at the second interval, t2.

3. The method of claim 1, wherein the second current measurement has a magnitude that is greater than a magnitude of the first current measurement when an insufficient quantity of fluid test sample has been introduced to the electrochemical test sensor.

4. The method of claim 1, further comprising:

after the second time period, applying a third potential between the counter electrode and the working electrode for a third predetermined time period;

measuring the current between the counter electrode and the working electrode at a third interval during the third predetermined time period to obtain a third current measurement;

measuring the current between the counter electrode and the working electrode at a fourth interval during the third predetermined time period to obtain a fourth current measurement;

determining a second parameter based on the third current measurement and the fourth current measurement;

comparing a second parameter to at least one second predetermined parameter; and notifying a user that an insufficient quantity of fluid test sample has been introduced to the electrochemical test sensor based on the comparing the second parameter to the at least one second predetermined parameter.

5. The method of claim 4, wherein the second parameter is determinable by a calculation having the general form $$\text{second parameter} = \ln(I_{t3}) - \ln(I_{t4})/(\ln(t4) - \ln(t3))$$

where $I_{t3}$ is the third current measurement at the third interval, t3, and $I_{t4}$ is the fourth current measurement at the fourth interval, t4.

6. The method of claim 4, wherein the first predetermined time period and the second predetermined time period comprise a burn period, the third predetermined time period comprises a read period, and no potential is applied between the counter electrode and the working electrode for a wait period, the wait period being after the burn period and prior to the read period.

7. The method of claim 4, wherein the first predetermined time period and the second predetermined time period comprise a first pulse period, and the third predetermined time period comprises a second pulse period.

8. A method for evaluating whether an electrochemical test sensor is properly filled, the test sensor including a working electrode electrically coupled to a first lead and a counter electrode electrically coupled to a second lead, the counter electrode including a low-resistance portion and a high-resistance portion, the high-resistance portion including a resistor, the method comprising:

applying a voltage profile across the first and second leads;

measuring the current profile at the first and second leads in response to the applied voltage profile;

comparing the measured current profile to a predetermined current profile; and generating an under-filled error signal based on the comparing of the measured current profile to the predetermined profile.

9. The method of claim 8 wherein the predetermined profile is a decay-shaped profile.

10. The method of claim 8 comprising forming an electrical communication between only the high-resistance portion of the counter electrode and the working electrode when the test sensor is under-filled.

11. The method of claim 8 comprising forming an electrical communication between the low-resistance and high-resistance portions of the counter electrode and the working electrode when the test sensor is appropriately-filled.

12. The method of claim 8 wherein the fluid test sample comprises blood.

13. The method of claim 8 wherein the analyte comprises glucose.

14. A method for evaluating whether an electrochemical sensor is properly filled, the test sensor including a working electrode coupled to a first lead, and counter electrode coupled to a second lead, the counter electrode including a high-resistance portion and a low-resistance portion, the high-resistance portion including a resistor, the test sensor including a reagent disposed on the working electrode that is adapted to react with glucose in a blood sample for producing an electrochemical reaction indicative of the concentration of the glucose in the blood sample, the method comprising:

collecting a blood sample;

applying a voltage profile across the first and second leads;

measuring the current profile at the first and second leads in response to the applied voltage profile; and generating an under-filled error signal when the measured current profile is not of a predetermined shape.

15. The method of claim 14 wherein the predetermined shape is a decay-shaped.

16. The method of claim 14 comprising forming an electrical communication between only the high-resistance portion of the counter electrode and the working electrode when the test sensor is under-filled.

17. The method of claim 14 comprising forming an electrical communication between the low-resistance portion of the counter electrode and the working electrode when the test sensor is appropriately-filled.

18. The method of claim 14 wherein the reagent comprises glucose oxidase.

19. The method of claim 14 wherein the reagent is also disposed on the low-resistance portion of the counter electrode.

20. The method of claim 14, wherein the resistor is screen printed on an insulating base of the test sensor.

21. The method of claim 14, wherein the reagent is also disposed on the high-resistance portion.

22. The method of claim 14, wherein the test sensor includes a flow path for receiving the blood sample, the low-resistance portion of the counter electrode is disposed along the flow path downstream from the working electrode, and the high-resistance portion of the counter electrode is disposed along the flow path upstream from the working electrode.

23. A method for evaluating whether an electrochemical sensor is properly filled, the test sensor including a working electrode coupled to a first lead, and counter electrode coupled to a second lead, the counter electrode including a high-resistance portion and a low-resistance portion, the high-resistance portion including a resistor, the method comprising:

collecting a blood sample;

applying a first potential across the first and second leads for a first predetermined time period;

after the first predetermined time period, applying a second potential across the first and second leads for a second predetermined time period, the second potential having a magnitude that is greater than a magnitude of the first potential; and measuring the current at the first and second leads at least one interval in response to the applied first potential and the applied second potential.

24. The method of claim 23, further comprising generating an under-filled error signal based on the measured current.

* * * * *